Sept. 16, 1975 J. C. MIKKELSEN Plant Pat. 3,785
BEGONIA PLANT
Filed Aug. 19, 1974
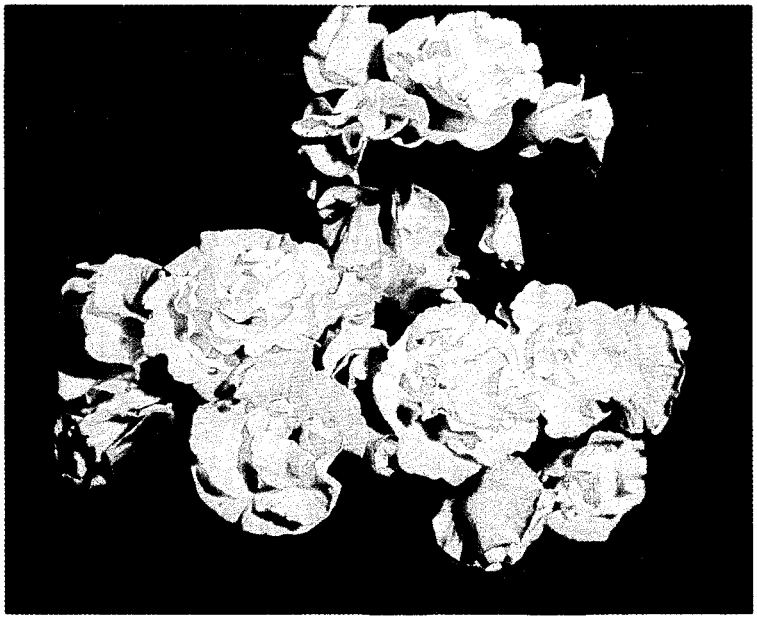

United States Patent Office

Plant Pat. 3,785
Patented Sept. 16, 1975

3,785
BEGONIA PLANT

James C. Mikkelsen, Ashtabula, Ohio, assignor to Mikkelsens Inc., Ashtabula, Ohio Filed Aug. 19, 1974, Ser. No. 498,866
Int. Cl. A01h 5/00
U.S. Cl. Plt.—68 1 Claim The present invention relates to a new and distinctive variety of begonia plant, known by the varietal name Mikkel Limelight and botanically known as *Begonia elatior* (B × *hiemalis*—Fotsch). The new cultivar was discovered by me as a result of successive mutation events from the parent variety Aphrodite Pink, disclosed in U.S. Plant Pat. 3,318, issued Mar. 13, 1974, to Otto Rieger. The parent cultivar Aphrodite Pink mutated an axillary shoot that had whitish flowers with pink streaks. This shoot was rooted and cuttings were taken continuously, rooted and flowered. After considerable time and numbers of propagations, clear white flowers began to appear. Stem cuttings and leaf cuttings propagated from the clear white flowering plants have continued to come true to type as illustrated in the accompanying photographic drawing.

The following characteristics distinguish the new begonia from both its parent and other begonias commercially known and used in the floriculture industry:

1. Clear white, ruffled edge, double azalea type flowers with light chartreuse infusion on the back side of tepals.
2. This is the first white Aphrodite type known to be found, and provides a needed color in the Aphrodite begonia family.
3. Growth characteristics similar to parent variety. Stems have sufficient vigor that some staking will allow the new variety to be grown as an upright.
4. Foliage is lighter green compared to parent. Size of leaf is comparable to parent.
5. Because of the urgency for intensive propagation to purify the color it was simultaneously determined that the new variety also propagates quite well from leaf cuttings, at least well enough to use leaf cuttings fall, winter and spring. High light and temperature during summer apparently inhibits initiation of adventitious buds.

The accompanying colored photographic drawing particularly illustrates the unique flower color of the new variety, with the colors being as true as reasonably possible to obtain in a colored reproduction of this type.

The following is a detailed description of my new begonia variety based on plants produced under commercial practices in Ashtabula, Ohio. Color references are made to the Royal Horticultural Society Colour Chart except where general color terms of ordinary dictionary significance are used.

*Parentage*: Several step mutations from the parent cultivar Aphrodite Pink.

*Propagation*: Stem cuttings at anytime rooting in 25–28 days at 20°–22° C.; by leaf cuttings in fall, winter, and spring months in Ashtabula, Ohio.

*Rooting Habit*: Rapid, fine—dendritic.

*Plant Form*: Bushy.

*Habit of Growth*: Nearly upright—some tendency to be slightly procumbent.

*Blooming Habits*: Blooming is profuse and continues over a period of four to six months after flowers are initiated. Flowering delayed under high light and temperature environments. Flowering can be manipulated year round by proper environmental management.

*Blooming Season*: Normal blooming season is late November based on cuttings propagated during summer months.

*Foliage*: Abundant, borne on slight angle to main stem; good resistance to mildew.

- *Size*—Ten to twelve cm. in diameter.
- *Shape*—Heart shape to oval.
- *Texture*—Smooth, waxy.
- *Margin*—Very little sinus indention, some serration on young leaves.
- *Color*—New: top, 146B–C; under, 147C. Mature: top, 148A; under, 148C.

*Disease Resistance*: Resistance over all is quite good, especially to common powdery mildew.

*Flowers*:

- *Borne*—Continuously on trusses for periods of five to six months.
- *Quantity*—Average for this type except under high light/temperature environments when flowering is inhibited.
- *Buds*—Flat, round, 10–15 mm. in diameter before opening.
- *Tepals*—White with chartreuse infusion on back side of tepals.
- *Reproductive Organs*: Stamens—None seen to date. Pollen—None seen to date. Styles/ovaries—None seen to date.

I claim:

1. A new and distinct cultivar of begonia characterized particularly by its clear white, ruffled edge, double azalea type flowers having light chartreuse infusion on the back side of the tepals; its profuse blooming habit and by its ease of propagation both by stem and leaf cuttings.

No references cited.

ROBERT E. BAGWILL, Primary Examiner